(12) United States Patent
Braden et al.

(10) Patent No.: US 9,023,395 B2
(45) Date of Patent: May 5, 2015

US009023395B2

(54) FORMULATION OF ACTIVE AGENT LOADED ACTIVATED PLGA NANOPARTICLES FOR TARGETED CANCER NANO-THERAPEUTICS

(75) Inventors: Arthur R. C. Braden, Arlington, TX (US); Jamboor K. Vishwanatha, Fort Worth, TX (US)

(73) Assignee: University of North Texas Health Science Center at Fort Worth, Fort Worth, TX (US)

( * ) Notice: Subject to any disclaimer, the term of this patent is extended or adjusted under 35 U.S.C. 154(b) by 0 days.

(21) Appl. No.: 12/101,929

(22) Filed: Apr. 11, 2008

(65) Prior Publication Data

US 2008/0253961 A1     Oct. 16, 2008

Related U.S. Application Data

(60) Provisional application No. 60/911,528, filed on Apr. 13, 2007.

(51) Int. Cl.
| | | |
|---|---|---|
| *A61K 9/14* | (2006.01) | |
| *A61K 51/00* | (2006.01) | |
| *A61K 31/045* | (2006.01) | |
| *A61M 36/14* | (2006.01) | |
| *A01N 31/00* | (2006.01) | |
| *A61K 31/70* | (2006.01) | |
| *A61K 9/16* | (2006.01) | |
| *A61K 9/51* | (2006.01) | |
| *A61K 47/48* | (2006.01) | |
| *B82Y 5/00* | (2011.01) | |

(52) U.S. Cl.
CPC ............... *A61K 31/70* (2013.01); *A61K 9/167* (2013.01); *A61K 9/5153* (2013.01); *A61K 9/5192* (2013.01); *A61K 47/48907* (2013.01); *A61K 47/48915* (2013.01); *B82Y 5/00* (2013.01)

(58) Field of Classification Search
None
See application file for complete search history.

(56) References Cited

U.S. PATENT DOCUMENTS

| | | | |
|---|---|---|---|
| 5,049,322 A | 9/1991 | Devissaguet | |
| 6,395,253 B2 | 5/2002 | Levy | |
| 6,482,439 B2* | 11/2002 | Prokop | 424/489 |
| 6,814,980 B2 | 11/2004 | Levy | |
| 6,953,645 B2 | 10/2005 | Kim et al. | |
| 2004/0157330 A1 | 8/2004 | Sheridan | |
| 2004/0220081 A1 | 11/2004 | Kreitz | |
| 2005/0037075 A1 | 2/2005 | Farokhzad et al. | |
| 2005/0196343 A1* | 9/2005 | Reddy et al. | 424/9.322 |
| 2005/0266090 A1 | 12/2005 | Prokop | |
| 2005/0287218 A1* | 12/2005 | Chaouk et al. | 435/486 |
| 2005/0287639 A1* | 12/2005 | Kwon et al. | 435/69.1 |
| 2006/0067925 A1 | 3/2006 | Labhasetwar | |
| 2006/0067998 A1* | 3/2006 | Kurzrock et al. | 424/450 |
| 2006/0134209 A1 | 6/2006 | Labhasetwar | |
| 2006/0228414 A1* | 10/2006 | Cook | 424/469 |
| 2006/0281076 A1* | 12/2006 | Marla et al. | 435/5 |
| 2007/0082838 A1 | 4/2007 | De | |
| 2007/0098802 A1 | 5/2007 | Farr | |
| 2010/0015051 A1* | 1/2010 | Labhasetwar et al. | 424/1.69 |

OTHER PUBLICATIONS

Sahoo et al. International Journal of Cancer 2004 112:335-340.*
Chendil et al. Oncogene 2004 23:1599-1607.*
Vandervoort et al. International Journal of Pharmaceutics 2002 238:77-92.*
Keegan et al. Macromolecules 2004 37:9779-9784.*
Kocbek et al. Journal of Controlled Release 2007 120:18-26.*
Labhasetwar et al. Journal of Pharmaceutical Sciences 1998 87:1229-1234.*
Nylander-French et al. In Vitro Cellular and Developmental Biology—Animal 2000 36:611-616.*
Hans et al. Current Opinion in Solid State and Materials Science 2002 6:319-327.*
International Search Report and Written Opinion for PCT/US2008/060142 dated Jul. 7, 2008.
Farokhzad, O. C., et al., "Targeted nanoparticle-aptamer bioconjugates for cancer chemotherapy in vivo," Proc Nail Acad Sci USA (2006), 103:6315-6320.
Horoszewicz, J.S., et al, "Monclonal Antibodies to a New Antigenic Marker in Epithelial Prostatic Cells and Serum of Prostatic Cancer Patients," Anticancer Research, 1987, 7:927-936.
Sokoloff, et al, "Quantificatino of prostate specific membrane antigen (PSMA) in human tissues and subcellular fractions," Proc. Am. Assoc. Cancer Res., 1998, 39:265.
Freitas, S., et al., "Microencapsulation by solvent extraction/evaporation: reviewing the state of the art of microsphere preparation process technology," Journal of Controlled Release (2005) 102:313-332.
Ong, H. T., et al., "Exploiting the high-affinity phosphonate-hydroxyapatite nanoparticle interaction for delivery of radiation and drugs." J Nanopart Res (2008) 10:141-150.
Shaikh, J., et al., "Nanoparticle encapsulation improves oral bioavailability of curcumin by at least 9-fold when compared to curcumin administered with piperine as absorption enhancer." European Journal of Pharmaceutical Sciences (2009) 37:223-230.

(Continued)

*Primary Examiner* — Juliet Switzer
*Assistant Examiner* — Caralynne Helm
(74) *Attorney, Agent, or Firm* — Chainey P. Singleton; Edwin S. Flores; Chalker Flores, LLP (57) ABSTRACT

The present invention includes compositions and methods of making an activated polymeric nanoparticle for targeted drug delivery that includes a biocompatible polymer and an amphiphilic stabilizing agent non-covalently associated with a spacer compound that includes at least one electrophile that selectively reacts with any nucleophilic on a targeting agent and places the targeting agent on the exterior surface of a biodegradable nanoshell, wherein an active agent is loaded with the nanoshell.

11 Claims, 5 Drawing Sheets

(56) References Cited

OTHER PUBLICATIONS

Yamamoto, H., et al., "Surface-modified PLGA nanosphere with chitosan improved pulmonary delivery of calcitonin by mucoadhesion and opening of the intercellular tight junctions." Journal of Controlled Release (2005) 102:373-381.
Zweers, M., et al., "In vitro degradation of nanoparticles prepared form polymers based on DL-lactide, glycolide and poly(ethylene oxide)." Journal of Controlled Release (2004) 100:347-356.
Bala, I., et al., "PLGA Nanoparticles in Drug Delivery: The State of the Art." Crit Rev Thera Drug Carrier Sys (2004), 21:387-422.
Bander, N.H., et al., "Targeting metastatic prostate cancer with radiolabeled monoclonal antibody J591 to the extracellular domain of prostate sepcific membrane antigen." J Urol. (2003), 170:1717-1721.
Barrett, A.J., "Nomenclature committee of the international union of biochemistry and molecular biology (NC-IUBMB). enzyme nomenclature." Eur J Biochem. (1997), 250:1-6.
Beer, T.M., et al., "Interim results from ASCENT: A double-blinded randomized study of DN-101 (high dose calcitrol) plus docetaxel vs. placebo plus docetaxel in androgen-independent prostate cancer." ASCO Meeting Abstract. (2005), 23:4516.
Bilati, U., et al., "Development of a nanoprecipitation method intended for the entrapment of hydrophilic drugs into nanoparticles." Eur J Pharm Sci (2005), 25:67-75.
Bisht, S., et al., "Polymeric nanoparticle-encapsulated curcumin ("nanocurcumin"): a novel strategy for human cancer therapy." J Nanobiotech (2007) 5:3 (18 pages).
Bossy-Nobs, L., et al., "Coupling Methods to Obtain Ligand-Targeted Liiposomes and Nanoparticles," Drugs and the Pharmaceutical Sciences (2006), 158:123-148.
Bostwick, D.G., et al., "Prostate-specific membrane antigen expression in prostatic intraepithelial neoplasia and adenocarcinoma: A study of 184 cases." Cancer (phila ). (1998), 82:2256-2261.
Chang, S.S., et al., "Five different anti-prostate-specific membrane antigen (PSMA) antibodies confirm PSAM expression in tumor-associated neo-vasculature." Cancer Res. (1999), 59(13):3192-3198.
Chang, S.S.. "Prostate-specific membrane antigen is produced in tumor-associated neovasculature." Clin Cancer Res (1999), 5:2674-2681.
Chang, S.S.. "Overview of prostate-specific membrane antigen." Reviews in Urology. (2004), 6(10):S13-18.
Cheng, J., et al., "Formulation of functionalized PLGA-PEG nanoparticles for in vivo targeted drug delivery," Biomaterials (2007), 28:869-876.
Chiang, Y., et al., "Specific down-regulation of annexin II expression in human cells interferes with cell proliferation," Mol Cell Biochem (1999), 199:139-147.
D'Souza, R. D., et al., "Curcumin-loaded PLGA Microspheres with Enhanced Radioprotection in Mice," Pharmaceutical Sciences (1997), 3:439-441.
Des Rieux, A., et al., "Nanoparticles as potential oral delivery systems of proteins and vaccines: A mechanistic approach," J Controlled Release (2006), 116:1-27.
Figg, W.D., et al., "A randomized phase II trial of thalidomide, an angiogenesis inhibitor, in patients with androgen-independent prostate cancer." Clin Cancer Res. (2001), 7:1888-1893.
Israeli, R., et al., "Expression of the prostate-specific membrane antigen." Cancer Res. (1994), 54:1807-1811.
Israeli, R., et al., "Molecular cloning of a complementary DNA encoding a prostate-specific membrane antigen.", Cancer Res. 1993 53:227-230.

Jain, R. A., "The manufacturing techniques of various drug loaded biodegradeable poly(lactide-co-glycolide) (PLGA) devices," Biomaterials (2000), 21:2475-2490.
Kawakami, M., et al., "Enhanced expression of prostate-specific membrane antigen gene in prostate cancer as revealed by in situ hybridization." Cancer Res. (1997), 57:2321-2324.
Kumar, M.N.V. R., et al., "Polymeric Nanoparticles for Drug and Gene Delivery," Encyclopedia of Nanoscience and Nanotechnology (2004), 9:1-19.
Labhasetwar, V., "Nanotechnology for drug and gene therapy: the importance of understanding molecular mechanisms of delivery," Curr Op Biotech (2005), 16:674-680.
Liu, H. et al., "Monoclonal antibodies to the extracellular domain of prostate-specific membrane antigen also react with tumor vascular endothelium." Cancer Res. (1997), 57:3629-3634.
Lopes, A.D., et al., "Immunohistochemical and pharmacokinetic characterization of the site-specific immunoconjugate CYT-356 derived from antiprostate monoclonal antibody 7E11-C5." Cancer Res. (1990), 50:6423-6429.
Mitra, A., et al., "Nanocarriers for Nuclear Imaging and Radiotherapy of Cancer," Curr Pharm Design (2006), 12:4729-4749.
Pan, C.J., et al., "Preparation, charachterization and anticoagulation of curcumin-eluting controlled biodegradable coating stents," J Controlled Release (2006), 116:42-49.
Panyam, J., et al., "Rapid endo-lysosomal escape of poly(DL-lactide-co-glycolide) nanoparticles: Implications for drug and gene delivery." FASEB J. (2002), 16:1217-1226.
Panyam, J., et al., "Biodegradable nanoparticles for drug and gene delivery to cells and tissue." Adv Drug Deliv Rev. (2003), 55:329-347.
Panyam, J., et al., "Fluorescence and electron microscopy probes for cellular and tissue uptake of poly(D,L-lactide-co-glycolide) nanoparticles." Int J Pharm. (2003), 262:1-11.
Prabha, S., et al., "Critical Developments in PLGA/PLA Nanoparticle-Mediated Gene Expression," Pharmaceutical Research (2004), 21:354-364.
Sahoo, S.K., et al., "Nanotech approaches to drug delivery and imaging," Drug Discovery Today (2003), 8:1112-1120.
Sahoo, S.K., et al., "Efficacy of transferrin-conjugated paclitaxel-loaded nanoparticles in a murine model of prostate cancer." Int J Cancer. (2004), 112:335-340.
Sahoo, S.K., et al., "Enhanced Antiproliferative Activity of Transferrin-Conjugated Paclitaxel-Loaded Nanoparticles is Mediated via Sustained Intracellular Drug Retention," Molecular Pharmaceutics (2005), 2:373-383.
Singh, S., "From Exotic Spice to Modern Drug?" Cell (2007), 130:765-768.
Smith-Jones, P.M., et al., "Radiolabeled monoclonal antibodies specific to the extracellular domain of prostate-specific membrane antigen: Preclinical studies in nude mice bearing LNCaP human prostate tumor." J Nuc Med. (2003), 44:610-617.
Stix, G., "Spice Healer," Scientific American Magazine (2007), 296:66-69.
Sunderland, C. J., et al., "Targeted Nanoparticles for Detecting and Treating Cancer," Drug Development Research (2006), 67:70-93.
Wright, G.L., et al., "Expression of prostate-specific membrane antigen in normal, benign, and malignant prostate tissues." Urol Oncol. (1995), 1:18-28.
Wright, G.L., et al., "Upregulation of prostate-specific membrane antigen after androgen-deprivation therapy." Urology. (1996), 48:326-334.

\* cited by examiner

FORMULATION OF ACTIVE AGENT LOADED ACTIVATED PLGA NANOPARTICLES FOR TARGETED CANCER NANO-THERAPEUTICS

CROSS-REFERENCE TO RELATED APPLICATIONS

This application claims priority to U.S. Provisional Application Ser. No. 60/911,528, filed Apr. 13, 2007, the entire contents of which are incorporated herein by reference.

TECHNICAL FIELD OF THE INVENTION

The present invention relates in general to the field of active agent loaded particles, and more particularly, to compositions and methods for delivering active agents in PLGA loaded particles.

STATEMENT OF FEDERALLY FUNDED RESEARCH

None.

BACKGROUND OF THE INVENTION

Without limiting the scope of the invention, its background is described in connection with the delivery of active pharmaceutical agents.

One of the greatest problems associated with molecular therapeutics is delivery of the therapeutic agent to the site of action. For the case of anti-cancer agents such as curcumin there is the necessity to keep the dose at minimal levels for the protection of the patient. The reduction in dose however; may not fully treat the disease. Thus, through the direction of a drug delivery device to a specific site of action via the conjugation of various antibodies more advantageous therapeutic regimes can be developed.

SUMMARY OF THE INVENTION

The present invention includes compositions and methods of making an activated polymeric nanoparticle for targeted drug delivery that includes a biocompatible polymer and an amphiphilic stabilizing agent non-covalently associated with a spacer compound containing at least one electrophile that selectively reacts with any nucleophile on a targeting agent and places the targeting agent on the exterior surface of a biodegradable nanoshell, wherein an active agent is loaded with the nanoshell. In some embodiments, the nanoshell includes one or more polyesters and one or more amphiphilic stabilizing agents. The polyester is poly-lactic acid, poly-glycolic acid, poly-lactic-co-glycolic acid, and combinations thereof. In one embodiment, the amphiphilic stabilizing agent is a polyol, e.g., the polyol is polyvinyl alcohol, polyethylene glycol, polypropylene glycol, polypropylenediol, polytetrahydrofuran, and combinations thereof. The nanoshell may encapsulate an active agent, such as a plasmid DNA, siRNA, proteins, small molecules, or anti-cancer agents (e.g., paxlitaxel, curcumin) for controlled intracellular delivery. Using the present invention, the nanoshell composition is used to control the ultimate size and drug delivery rate and/or a targeting agent that selectively targets the nanocarrier to diseased tissue/cells, thereby minimizing whole body dose.

The nanoshell may be loaded with an active agent that combines a conventional radioisotopes and a chemotherapeutic. In another embodiment, the nanoshell is adapted for controlled release of the active agents by pre-determining the polymeric ratios of lactic to glycolic acid. The nanoparticle may also include a spacer compound that is spacer is homofunctional, heterofunctional, multifunctional, monoreactive, bi-reactive or multireactive, water soluble, water-insoluble or partially water soluble. Examples of targeting agents for use with the present invention include an antibody, a small molecule, a peptide, a carbohydrate, a protein, a nucleic acid, an aptamer, a second nanoparticle, a cytokine, a chemokine, a lymphokine, a receptor, a lipid, a lectin, a ferrous metal, a magnetic particle, a linker, an isotope and combinations thereof. Other active agents may include an anti-cancer drug, an antibiotic, an antiviral, an antifungal, an antihelminthic, a nutrient, a small molecule, a siRNA, an antioxidant, and an antibody. In one specific example the active agent is an anti-cancer drug, e.g., curcumin or a derivative thereof.

The present invention also includes a method of making a targetable, loadable-nanoparticle by forming a first emulsion comprising a biocompatible polymer in a first solvent and an active agent by, e.g., mixing, sonication, vortexing or other blending; preparing a second solution comprising an amphiphilic stabilizing agent in water, a non-solvent used for control of the ultimate size of the nanoparticle and a spacer compound containing at least one electrophile; forming a second emulsion by mixing the first emulsion and the second solution by, e.g., sonication, vortexing or other blending methods to form activated, loaded nanoparticles with non-covalently associated spacer compounds; separating the activated, loaded nanoparticles; and binding a targeting agent to the particle at one or more electrophiles on the noncovalently associated spacer compounds. Examples of spacer compounds spacer is homofunctional, heterofunctional, multifunctional, monoreactive, bi-reactive or multireactive, water soluble, water-insoluble or partially water soluble. The targeting agent for the nanoparticle may be an antibody, a small molecule, a peptide, a carbohydrate, a protein, a nucleic acid, an aptamer, a second nanoparticle, a cytokine, a chemokine, a lymphokine, a receptor, a lipid, a lectin, a ferrous metal, a magnetic particle, a linker, an isotope and combinations thereof. Active agents for use with the method of the present invention include, e.g., an anti-cancer drug, an antibiotic, an antiviral, an antifungal, an antihelminthic, a nutrient, a small molecule, a siRNA, an antioxidant, and an antibody. The nanoshell may also include one or more polyesters and/or one or more amphiphilic stabilizing agents. Polyesters for use with the present invention may include poly-lactic acid, poly-glycolic acid, poly-lactic-co-glycolic acid, and combinations thereof. One non-limiting example of an amphiphilic stabilizing agent is, e.g., a polyol, polyvinyl alcohol, polyethylene glycol, polypropylene glycol, polypropylenediol, polytetrahydrofuran, poly(ethylene oxide)-poly(propylene oxide)-poly(ethylene oxide) (PEO-PPO-PEO) triblock copolymers, and combinations thereof. The nanoshell may encapsulate plasmid DNA, siRNA, proteins, small molecules or anti-cancer agents (e.g., paxlitaxel, curcumin) for controlled intracellular delivery and/or used to control the ultimate size and drug delivery rate. The targeting agent may selectively target the nanocarrier to diseased tissue/cells, thereby minimizing whole body dose and in some embodiments, it may be attached to radiolabeled conjugated antibodies on the surface of the nanoparticle. The nanoshell may be loaded with an active agent combines a conventional radioisotopes and a chemotherapeutic and/or adapted for controlled release of the active agents by pre-determining the polymeric ratios of lactic to glycolic acid. In one specific example the active agent is an anticancer drug, e.g., curcumin or a derivative thereof.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

Detailed methodology for the formulation of activated curcumin loaded nanoparticles for secondary conjugation of biologically active agents (e.g. antibodies).

Table 1 (below) shows formulation parameters for the generation of curcumin loaded nanoparticles. Nanoparticles were made using ethanol or methanol as a non-solvent. A decrease in loading efficiency is observed as the concentration of curcumin is increased. There is a minimal variation in the size of the nanoparticles. The inclusion of the active agent does not affect the size or loading capacity of the nanoparticles.

TABLE 1

| Solvent | Active agent | Antibody | Curcumin Concentration (mg/mL) | Loading Efficiency | Particle size (nm) |
|---|---|---|---|---|---|
| Ethanol | − | − | 0.0 | n/a | 144-409 |
| Ethanol | − | − | 0.5 | 98.4% | 121-331 |
| Ethanol | − | − | 1.0 | 96.4% | 144-331 |
| Ethanol | − | − | 2.0 | 91.3% | 144-486 |
| Methanol | − | − | 0.0 | n/a | 121-289 |
| Methanol | − | − | 0.5 | 96.9% | 121-409 |
| Methanol | − | − | 1.0 | 88.5% | 121-578 |
| Methanol | − | − | 2.0 | 82.3% | 144-578 |
| Ethanol | + | − | 0.0 | n/a | 121-344 |
| Ethanol | + | − | 1.0 | 95.2% | 121-344 |
| Ethanol | + | + | 1.0 | 94.8% | ? |

Figure 1:
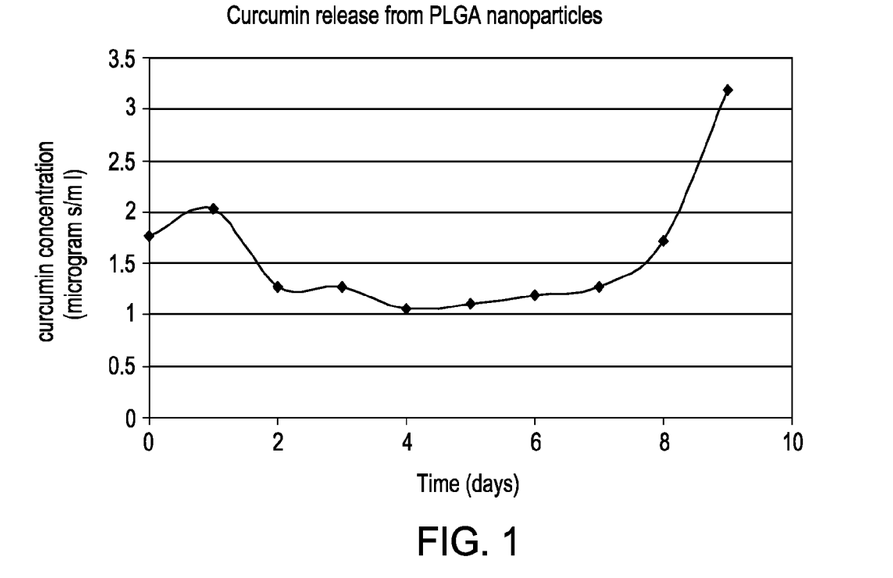
FIG. 1 is a graph that shows the Curcumin release from PLGA nanoparticles.

FIG. 1 is a graph that shows the rate of curcumin release from PLGA nanoparticles. 9 mg/mL of curcumin loaded nanoparticles were distributed into eppendorf tubes and placed on a rotisserie at 37° C. (final nanoparticle concentration of 1 mg/mL per tube). Daily measurements were taken for a period of 9 days. Curcumin concentration was determined by the absorbance at 430 nm.

Figure 2:
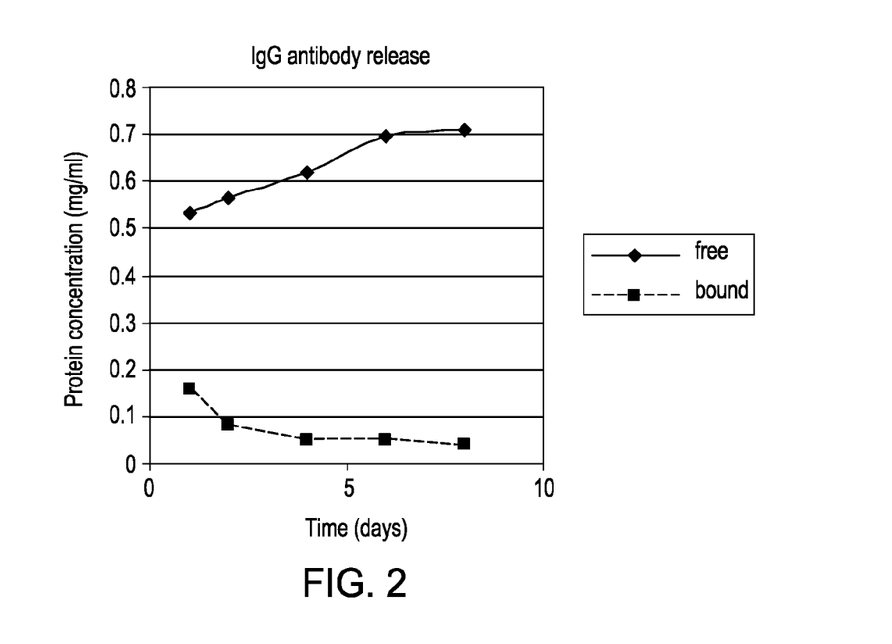
FIG. 2 is a graph of a calorimetric assay for antibody release from activated nanoparticles.

FIG. 2 is a graph of a colorimetric assay for antibody release from activated nanoparticles. 5 mg/mL of activated nanoparticles were conjugated to murine IgG. 1 mg aliquots were distributed into 1.5 mL eppendorf tubes and placed on a rotisserie at 37° C. At time points of 1, 3, 5, 7 and 9 days aliquots were removed for analysis. Antibody present in the supernatant (free antibody fraction) is seen to increase over the given time course. Antibody present within the nanoparticle fraction (bound non-covalently to the nanoparticle) is seen to decrease.

Figure 3:
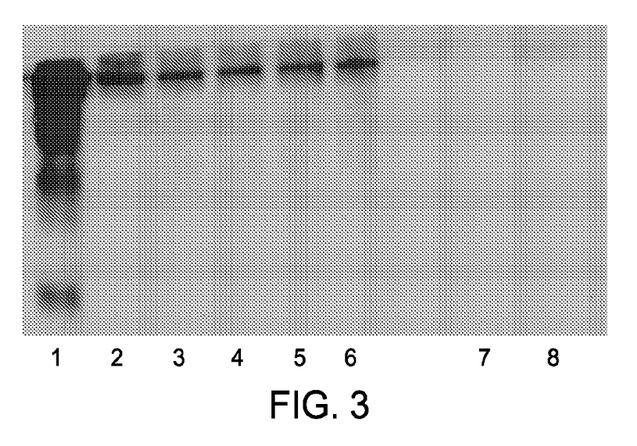
FIG. 3 is a Western blot analysis of the nanoparticle fraction from IgG conjugated nanoparticles.

FIG. 3 is a Western blot analysis of the nanoparticle fraction from IgG conjugated nanoparticles. Lane 1 represents native, denatured mouse IgG. Lanes 2-6 are IgG conjugated nanoparticles from time points of 1, 3, 5, 7 and 9 days respectively. Lane 7 represents unactivated nanoparticles. Lane 8 represents unconjugated active nanoparticles.

Figure 4:
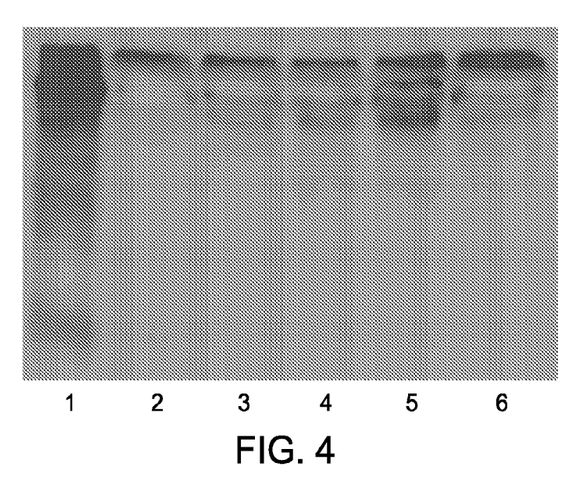
FIG. 4 is a Western blot analysis of the supernatant fraction from IgG conjugated nanoparticles.

FIG. 4 is also a Western blot analysis of the supernatant fraction (free antibody) from IgG conjugated nanoparticles. Lane 1 represents native, denatured mouse IgG. Lanes 2-6 are IgG conjugated nanoparticles from time points of 1, 3, 5, 7 and 9 days respectively.

Figure 5:
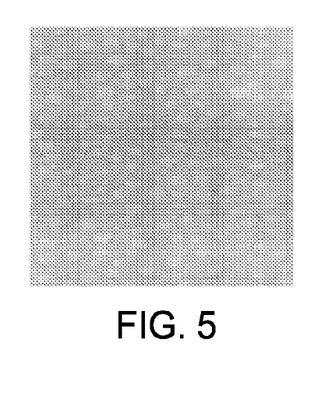
FIG. 5 is a Transmission Electron Micrograph (TEM image of BS$^3$ activated PLGA nanoparticles conjugated to murine Thy-1 antibody.

FIG. 5 is a TEM image of BS3 activated PLGA nanoparticles conjugated to murine Thy-1 antibody. Nanoparticles are visualized as white spherical globules. Murine Thy-1 antibody is visualized on the surface of the nanoparticles through reaction with anti-mouse colloidal gold labeled secondary antibody (seen as the black specks on the surface of the nanoparticles).

Figure 6:
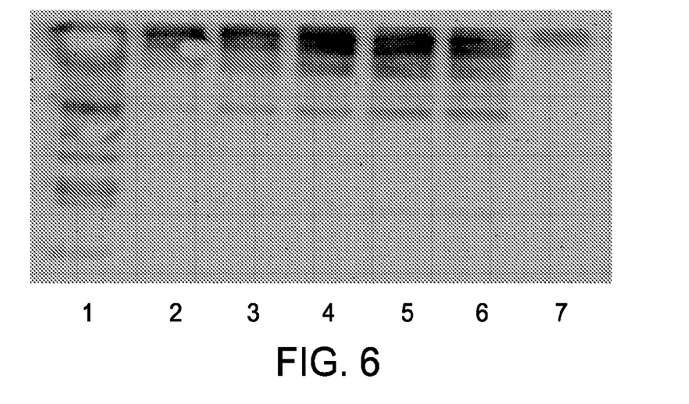
FIG. 6 is a Western blot analysis of Thy-1 labeled nanoparticles.

FIG. 6 shows a Western blot analysis of Thy-1 labeled nanoparticles. Lane 1 is native, denatured unconjugated murine Thy-1 shown at a concentration of 0.5 mg/mL. Lanes 2-6 represent increasing concentration of BS3 activated nanoparticles to which murine Thy-1 has been conjugated (11.5, 18.4, 23.0, 27.6, 34.5 µg of nanoparticles respectively). A linear increase in the presence of Thy-1 is observed as the concentration of nanoparticles is increased. Lane 7 represents activated nanoparticles indicating the migration of nanoparticles into the gel. The presence of a single band is indicative of the ability of the activated nanoparticles to selectively conjugate the secondary murine HRP antibody.

Figure 7A:
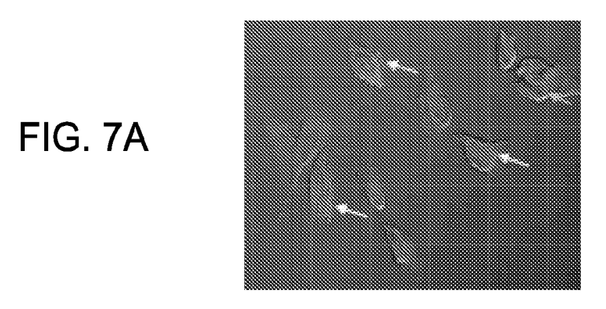
FIGS. 7A to 7C are micrographs of exposed retinal pigment epithelial cells to Thy-1 conjugated nanoparticles.
Figure 7B:
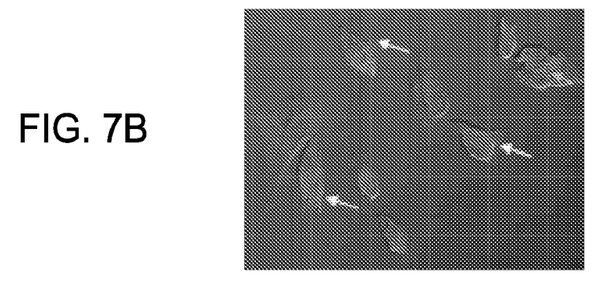
Figure 7C:
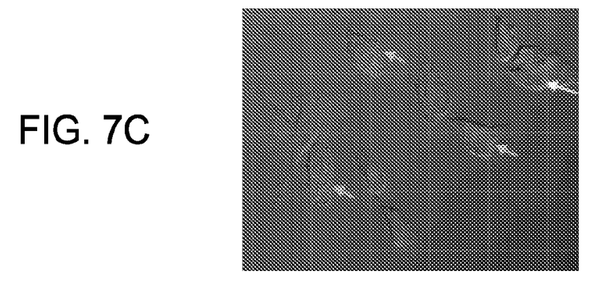

FIGS. 7A to 7C shows the effects of exposure of retinal pigment epithelial cells to Thy-1 conjugated nanoparticles. Nanoparticles were loaded with sulforhodamine 101 for visualization (red). Laser confocal microscopy using a z-stack was performed 90 minutes post exposure to targeted nanoparticles. FIGS. 7A, 7B, and 7C are orthogonal cross-sections at 8, and 13 micrometers within the cells. The yellow arrows indicate sites of nanoparticle concentration on the cell surface (red hot spots). The blue arrows indicate the absence of these hot spots as the focal place is increased or decreased.

Materials. Poly(D,L-lactide-co-glycolide) 50:50; i.v. 1.13 dL/g was purchased from Absorbable Polymers International (Pelham, Ala.). Poly(vinyl alcohol) M.W. 30,000-70,000, sulforhodamine 101, ethanol, methanol, and chloroform were purchased from Sigma-Aldrich (St. Louis, Mo.). Curcumin was a gift from Dr. Shubash Chauhan, South Dakota Medical Center. Thy-1 murine antibody was a gift from Dr. Neeraj Agarwal (UNTHSC at Fort Worth, Tex.). Mouse IgG was purchased from Promega (San Louis Obispo, Ca.).

Nanoparticle formulation. Nanoparticle formulation was carried out through a modified double emulsion technique. In this technique 30 mg of poly(D,L-lactide-co-glycolide) (PLGA) was first dissolved in 1 mL of chloroform at 4° C. Concurrently, 2 mL of a 2% w/v poly(vinyl alcohol) (PVA)/distilled deionized water solution was formed. Upon solubilization of the PVA in water, 1 mL of ethanol or methanol was added as a non-solvent to the PVA solution. The active agent bis-succinimidyl suberate (BS3) was then added to the PVA/ethanol solution at a concentration of 1 mM and stirred. A stock solution of 10 mg/ml curcumin was formed by the dissolution of curcumin into water under alkaline conditions using 0.5 M NaOH. Curcumin was added to the PLGA/Chloroform solution at concentrations of 0.5, 1.0, and 2.0 mg/mL per 150 microliters of aqueous volume. Formation of the primary emulsion was done by vortexing the curcumin-PLGA/chloroform solution for 20 seconds, followed by tip sonication at 55 W for 1 minute on a Branson Sonifier model W-350 (Branson, Danbury, Conn.). The primary emulsion was then added to the BS3/PVA/ethanol solution to initiate formation of the secondary emulsion. Completion of the secondary emulsion was done through vortexing for 20 seconds and tip sonication at 55 W for 2 minutes. Stabile activated nanoparticles were then aliquoted into 1.5 mL Eppendorf tubes and centrifuged for 5 minutes at 18,000 g. The chloroform and residual PVA supernatant was aspirated off and particles were resuspended by tip sonication in 1 mL of PBS pH 7.2. Following resuspension, nanoparticles were placed at −80° C. for 1 hour and lyophilized overnight. Lyophilization was carried out in an ATR FD 3.0 system (ATR Inc, St. Louis, Mo.) under a vacuum of 250 µT. After lyophilization nanoparticles were stored at 4° C. Upon use nanoparticles were weighed into eppendorf tubes and resuspended in 1 mL of PBS pH 7.2.

Size variations using alternate non-solvents are observed when nanoparticles were made with ethanol and methanol at the three concentrations. Greater than 90% entrapment was observed at concentrations of 1 mg/ml or less. There also appears to be a strong burst release. The observations made are in accordance with well known phenomenon regarding the release of small molecules from poly lactic-co-glycolic nanocarriers.

Conjugation of Thy-1 and IgG to the nanoparticle surface. To 5 mg of resuspended active nanoparticles, 250 microliters of murine Thy-1 (0.5 mg/ml) was added and the reaction was allowed to proceed overnight at 4° C. Nanoparticles were then either used immediately for study or were frozen at −20° C. to prevent significant breakdown of the PLGA polymer.

For the conjugation of murine IgG to the surface of the particle, 9 mg of activated nanoparticles were resuspended in PBS pH 7.2. Subsequently, 250 microliters of murine IgG (0.2 mg/mL) was then added and the reaction allowed to proceed at 4° C. overnight.

An activated polymeric nanoparticle was formulated to be used as a targeted drug delivery system. This system allows us to selectively attach any nucleophilic ligand (antibody, receptor proteins, localization sequences, organic molecules) to the exterior surface of a biodegradable nanoshell. The nanoshell is made from poly-lactic-co-glycolic acid an FDA approved polymer. Due to the properties of the nanoshell we can encapsulate plasmid DNA, siRNA, proteins, small molecules or chemotherapeutics (i.e. paxlitaxel and curcumin) for controlled intracellular delivery. We can also vary the formulation parameters of the nanoshell to control the ultimate size and drug delivery rate. Targeting of the nanocarriers allows for localization to the diseased tissue/cells thus minimizing whole body dose. It is also possible to radiolabel conjugated antibodies on the surface of the nanoparticle. This would allow for a combinatorial anti-cancer treatment strategy utilizing both conventional radioisotopes and chemotherapeutics. Controlled release of the therapeutic agents allows optimization of therapeutic strategies for different clinical maladies.

The compositions and methods of the present invention are versatile, allowing the user to select from a number of solvents to control the ultimate size of the nanoshell (for example, to improve cellular uptake properties for the nanoparticles, fairly well known to individuals skilled in the art of nanoparticles).

Control release properties were achieved by shifting the polymeric ratios of lactic to glycolic acid (known to those skilled in the art of nanoparticles). The particles are stabile when resuspended in isotonic buffers for a limited time or dehydrated at 4° C. indefinitely The present invention differs from existing technologies due to the fashion in which we target our particles. The most common method for the attachment of ligands to polymeric nanoparticles is through the grafting of poly ethylene glycol (PEG) to the PLGA polymeric strands thus making a PLGA-PEG copolymer. Linkage is performed to the PEG molecules using standard amine reactive chemistries. Our method generates an active particle for ligand attachment through the inclusion of a commercially available crosslinking agents (BS3, Pierce Biotechnology, Rockford, Ill.) present during the formation of the secondary emulsion. The BS3 present within the secondary emulsion solution is sequestered through hydrophobic/hydrophilic interactions between the PLGA emulsion and the PVA stabilizing agent also present in the secondary emulsion solution.

Another advantage of the compositions and methods of the present invention is that any biologically active molecule with a nucleophilic group can be attached to the nanoshells and/or nanoparticles through reaction against an exposed NHS ester moiety (i.e., electrophile), leading to an unlimited range of targeted particles for therapeutic purposes.

Role of prostate-specific membrane antigen (PSMA) as a cellular marker during the progression of prostate cancer: Prostate-specific membrane antigen (PSMA) is a type II integral membrane glycoprotein initially characterized by the mAb 7E11 in LNCaP cells. (11,12) PSMA consists of a short 18 amino acid intracellular segment, a transmembrane region composed of 24 amino acids, and an extensive extracellular C terminal domain of 706 amino acids. (13) The functional role of PSMA is currently under investigation, however; the structure of PSMA is identical to glutamate carboxypeptidase and folate hydrolase 1.

PSMA can be internalized upon antigen recognition. In correlation with prostate cancer progression, PSMA is highly expressed in benign prostate secretory-acinar epithelium, prostatic intraepithelial neoplasia (PIN) and prostate adenocarcinoma. Investigation of the expression levels of PSMA have found that expression is greatest in high grade PIN and in HRPC cancers. Thus, as prostate cancer progresses, PSMA expression has been shown to be increased, making targeted therapeutic applications for the treatment of prostate cancer based upon PSMA an attractive treatment option. An important factor associated with PSMA expression is that PSMA has been found to be expressed only on tumor-associated neovasculature but not on normal healthy vasculature. A coordinated expression between PSMA and VEGF has also been demonstrated. PSMA expression has also been observed on the vascular endothelium of other solid tumors such as breast, lung, ovary, kidney, bladder and intestinal tract.

Treatment options for prostate cancer: Following elevation of serum PSA levels and diagnosis of prostate cancer, clinical intervention begins. The primary form of intervention is the use of androgen ablation therapies. While these therapies have been shown to significantly reduce tumor volume there is a frequent recurrence of prostate cancer to a hormone refractory state. Traditional chemotherapeutics have also been used in the treatment of prostate cancer. Thalidomide has been shown to produce clinically effective results. However, it is a combination therapy using thalidomide with taxanes such as paclitaxel that has shown a more significant reduction in prostate tumor growth. A disadvantage to the use of thalidomide and paclitaxel however is limited water solubility. This requires higher doses of the therapeutic agents to serve as efficacious agents against prostate cancers. Recently, docetaxel has been shown to be an effective treatment option for prostate cancer. An attractive property of docetaxel is significantly improved water solubility. Use of nanoparticles as delivery vectors for either single chemotherapeutics or combinational two compound chemotherapeutic loaded nanoparticles (e.g., prednisone and taxanes) can easily be accomplished. In studies performed by Sahoo et al. conjugation of transferrin to paclitaxel containing nanoparticles demonstrated a five fold reduction in the $IC_{50}$.

Investigation was also conducted on the use of PSMA based antibody therapies. Radiolabelling of PSMA for the treatment of metastatic prostate cancer has demonstrated no systemic cytotoxicity and the ability to localize in vivo as well as to bony sites of metastatic disease. PSMA antibodies conjugated to toxins have been shown to be quickly internalized and have eradicated prostate tumors in mice without observations of toxicity. Thus, a combinatorial effect of docetaxel loaded nanoparticles targeted to sites of tumor vasculature using PSMA provides an attractive agent for the treatment of prostate cancer.

TABLE 2 includes various structures, linkers, payloads, functionality of the present invention.

| Linker name | | Chemical structure |
| --- | --- | --- |
| BS3 | Bis(sulfosuccinimidyl)suberate | |
| s-EGS | Ethylene glycobis-(sulfosuccinimidylsuccinate) | |
| DSG | Disuccinimidyl glutarate | |
| s-EMCS | N-[e-maleimidocaproyloxy] sulfosuccinimide ester | |
| BMPS | N-[b-maleimidopropyloxy] succinimide ester | |

TABLE 2-continued

| | Linker name | React-ivity | Function-ality | Select-ivity | Spacer Length (Å) | Solu-bility | Conjugates made | Payload |
|---|---|---|---|---|---|---|---|---|
| BM (PEO)₂ | 1,8-bismaleimidodi-ethyleneglycol | | | | | | | |
| PAS | Palmitic acid N-hydroxysuccin-imide ester | | | | | | | |
| BS3 | Bis(sulfosuccin-imidyl)suberate | Bi | Homo | 1° amines | 11.4 | H₂O | IgG Ab Thy-1 Ab | S101 Curcumin |
| s-EGS | Ethylene glycobis-(sulfosuccinimid-ylsuccinate) | Bi | Homo | 1° amines | 16.1 | H₂O | Anx A2 Ab PSMA Ab Transferrin | S101 docetaxel |
| DSG | Disuccinimidyl glutarate | Bi | Homo | 1° amines | 7.72 | DMSO | p21 Ab | S101 |
| s-EMCS | N-[e-maleimidocaproyl-oxy] sulfosuccinimide ester | Bi | Hetero | 1° amines Thiols | 9.4 | H₂O | VEGF R2 Ab Anx A2 Ab TNFa DTT | S101 Doxirubicin |
| BMPS | N-[b-maleimidopropyl-oxy] succinimide ester | Bi | Hetero | 1° amines Thiols | 5.9 | DMSO | Cytochrome C Ab DTT | S101 |
| BM (PEO)₂ | 1,8-bismaleimidodi-ethyleneglycol | Bi | Homo | Thiols | 14.7 | H₂O | PSMA Ab DTT | S101 |
| PAS | Palmitic acid N-hydroxysuccin-imide ester | Mono | n/a | 1° amines | ~18 | DMSO | IgG Ab | S101 |

Figure 8A:
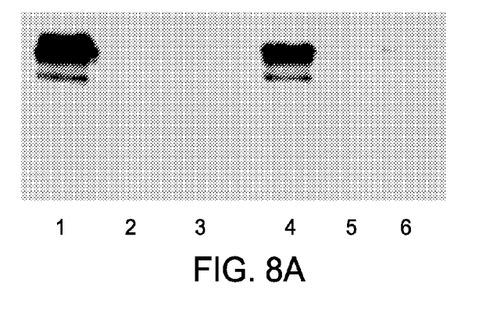
FIGS. 8A and 8B are Western Blots for variation of cross-linking reagents of the present invention.
Figure 8B:
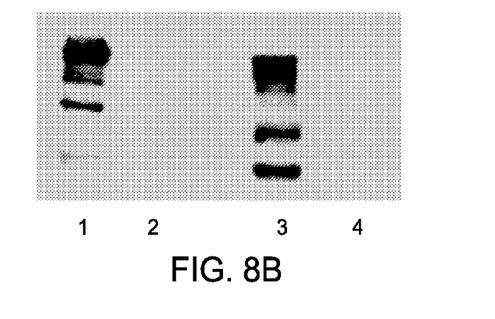
Figure 9A:
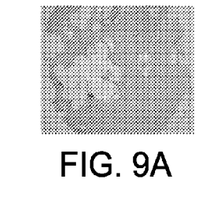
FIGS. 9A through 9H shows the PSMA expression in human prostate tissue sections using the present invention.
Figure 9B:
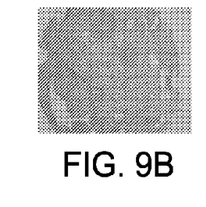
Figure 9C:
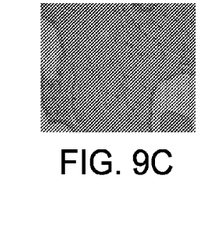
Figure 9D:
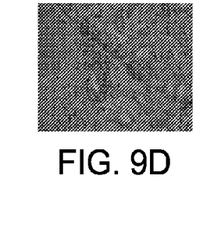
Figure 9E:
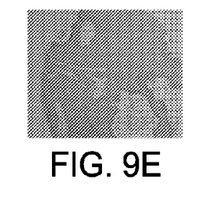
Figure 9F:
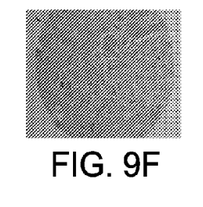
Figure 9G:
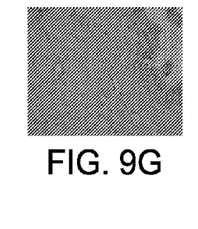
Figure 9H:
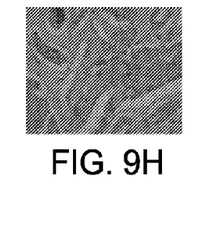

FIG. 8 is a Western Blot analysis for variation of cross-linking reagent: Panel A, lane 1 represents the use of DSG (water insoluble; homo-bifunctional amine reactive) for selective attachment of murine p21 antibody. Lane 2 represents activated DSG nanoparticles under quenched reaction conditions, note the absence of a detectable band. Lane 3 represents reaction with secondary HRP antibody used for detection of the conjugated reaction (original image displays a faint band). Lane 4 represents the incorporation of EGS (water soluble; homo-bifunctional amine reactive) for the attachment of murine annexin A2 antibody. Lane 5 is the activated EGS nanoparticles under quenched reaction conditions. Lane 6 represents activated EGS nanoparticles reacting with murine secondary HRP used for detection. Panel B: Lane 1 represents the use of BMPS (water insoluble; hetero-bifunctional for amines and sulfhydryls) for the conjugation of murine cytochrome C. Lane 2 is amine quenched BMPS activated nanoparticles. Lane 3 represents EMCS (water soluble; hetero bifunctional for amines and sulfhydryls) for the conjugation of rabbit VEGF receptor 2 antibody. Lane 4 displays quenched EMCS activated nanoparticles. For the instances of BMPS and EMCS due to the presence of only a single amine reactive site it is not possible to see the presence of secondary HRP reaction due to the extent of the reaction with the given targeting antibody. An increase in the concentration of activated nanoparticles would allow for visualization of the activated nanoparticle alone.

FIG. 9 is a PSMA expression in human prostate tissue sections. Human prostate microarray slides were probed with murine anti-PSMA antibody. Panels A and B represent high grade gleason scores for normal and cancerous regions respectively. Higher magnification images for these tissue samples are shown in panels C and D. Panels E and F represent low gleason scores for normal and cancerous regions respectively. Higher magnification images for these sections are shown in panels G and H. It is evident that PSMA expression in restricted to cancerous versus normal sections of the tumor mass and that as the gleason score increases there is greater expression of PSMA.

Figure 10:
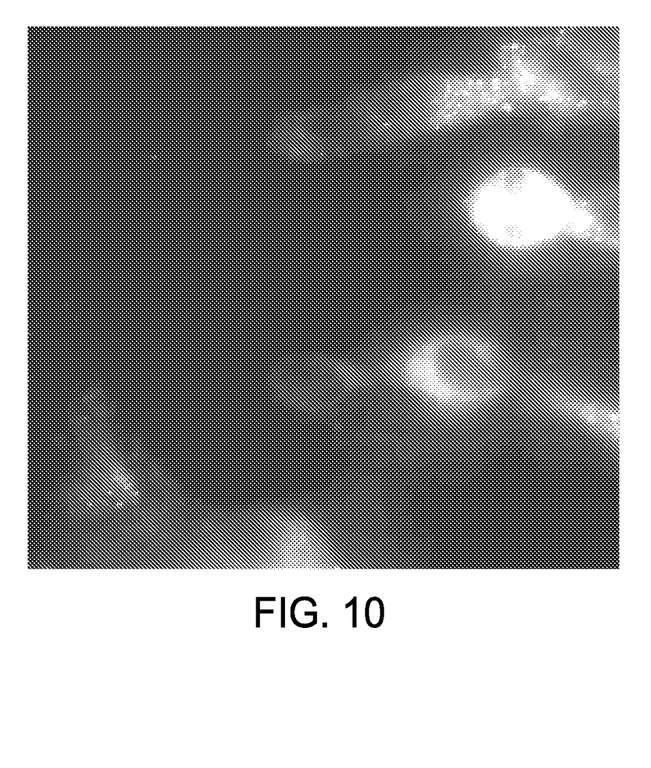
FIG. 10 is a TIRF analysis of zymed mouse anti-PSMA antibody specificity under co-culture conditions using the present invention.

FIG. 10 is a TIRF analysis of zymed mouse anti-PSMA antibody specificity under co-culture conditions. PC-3 cells were co-cultured with LNCaP C4-2 cells fixed for immuno-cytochemistry. It can be seen from the image that there is a significant amount of cellular reactivity for the LNCap C4-2 cell line and very limited cross reactivity with PC-3 cells. No cellular permeabilization steps were performed for this assay.

Figure 11A:
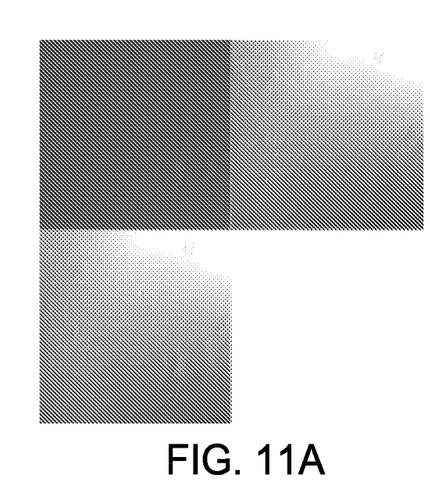
FIGS. 11A and 11B show the PSMA targeted nanoparticles display preferential uptake to LNCaP C4-2 cells over PC-3 cells using the present invention.
Figure 11B:
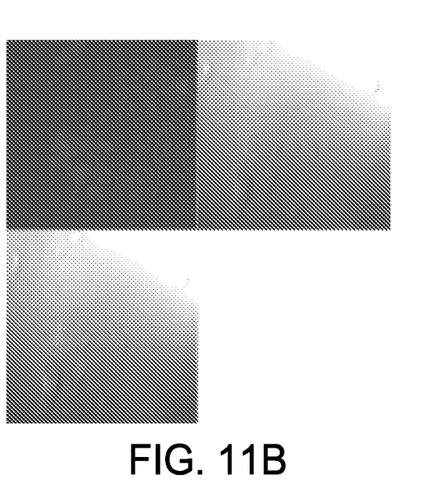

FIG. 11 is a PSMA targeted nanoparticles display preferential uptake to LNCaP C4-2 cells over PC-3 cells. Panel A, PSMA targeted nanoparticles were loaded with sulforhodamine 101 (red) and exposed to a co-culture of PC-3 and LNCaP C4-2 cells for 30 minutes under constant rocking motion. Samples were fixed in paraformaldehyde and visualized through laser confocal microscopy. PC-3 cells are shown with yellow arrows, LNCaP C4-2 cells are shown with green arrows. It is evident that there is a preferential uptake of targeted nanoparticles to the LNCaP C4-2 cell line. Panel B, Activated nanoparticles loaded with sulforhodamine 101 were quenched to prevent ligand attachment and exposed to identical co-culture conditions as in panel A. There is no apparent difference in cellular uptake for either PC-3 or LNCaP C4-2 cells.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

Israeli R, Powell C T, Fair W R, Heston W D. Molecular cloning of a complementary DNA encoding a prostate-specific membrane antigen. Cancer Res. 1993; 53:227-230.

Horoszewicz J S, Kawinski E, Murphy G p. Monoclonal antibodies to a new antigenic marker in epithelial cells and serum of prostate cancer patients. Anticancer Res. 1987; 7:927-936.

Lopes A D, Davis W L, Rosenstraus M J, Uveges A J, Gilman S C. Immunohistochemical and pharmacokinetic characterization of the site-specific immunoconjugate CYT-356 derived from antiprostate monoclonal antibody 7E11-C5. Cancer Res. 1990; 50:6423-6429.

Sokoloff R, Norton K C, Gasior C L, Marker K M, Grauer L S. Quantification of prostate specific membrane antigen (PSMA) in human tissues and subcellular fractions. Proc Am Assoc Cancer Res. 1998; 39:265.

Wright G L, Haley C, Beckett M L, Schellhammer P F. Expression of prostate-specific membrane antigen in normal, benign, and malignant prostate tissues. Urol Oncol. 1995; 1:18-28.

Bostwick D G, Pacelli A, Blute M, Roche P, Murphy G p. Prostate-specific membrane antigen expression in prostatic intraepithelial neoplasia and adenocarcinoma: A study of 184 cases. Cancer (phila). 1998; 82:2256-2261.

Kawakami M, Nakayama J. Enhanced expression of prostate-specific membrane antigen gene in prostate cancer as revealed by in situ hybridization. Cancer Res. 1997; 57:2321-2324.

Wright G L, Grob B M, Haley C, Grossman K, Newall K, Petrylak D, et al. Upregulation of prostate-specific membrane antigen after androgen-deprivation therapy. Urology. 1996; 48:326-334.

Chang S S, O'Keef D S, Bacich D J, Reuter V E, Heston W D, Gaudin P B. Prostate-specific membrane antigen is produced in tumor-associated neovasculature. Clin Cancer Res. 1999; 5:2674-2681.

Chung L, Isaacs W B, Simons J w, editors. Prostate cancer: Biology, genetics, and the new therapeutics.; 2001.

Chang SS, Reuter V E, Heston W D, Bander N H, Grauer L S, Gaudin P B. Five different anti-prostate-specific membrane antigen (PSMA) antibodies confirm PSAM expression in tumor-associated neo-vasculature. Cancer Res. 1999; 59(13):3192-3198.

Liu H, Moy P, Kim S, Xia Y, Rajasekaran A, Navarro V, et al. Monoclonal antibodies to the extracellular domain of prostate-specific membrane antigen also react with tumor vascular endothelium. Cancer Res. 1997; 57:3629-3634.

Israeli R, Powell C T, Corr J G, Fair W R, Heston W D. Expression of the prostate-specific membrane antigen. Cancer Res. 1994; 54:1807-1811.

Barrett A J. Nomenclature committee of the international union of biochemistry and molecular biology (NC-IUBMB). enzyme nomenclature. Eur J Biochem. 1997; 250:1-6.

Panyam J, Labhasetwar V. Biodegradable nanoparticles for drug and gene delivery to cells and tissue. Adv Drug Deliv Rev. 2003; 55:329-347.

Panyam J., Sahoo S. K., Prabha S., Bargar T., Labhasetwar V. Fluorescence and electron microscopy probes for cellular and tissue uptake of poly(D,L-lactide-co-glycolide) nanoparticles. Int J Pharm. 2003; 262:1-11.

Panyam J., Zhou W. Z., Prabha S., Sahoo S. K., Labhasetwar V. Rapid endo-lysosomal escape of poly(DL-lactide-co-glycolide) nanoparticles: Implications for drug and gene delivery. FASEB J. 2002; 16:1217-1226.

Figg W D, Dahut w, Duray P. A randomized phase II trial of thalidomide, an angiogenesis inhibitor, in patients with androgen-independent prostate cancer. Clin Cancer Res. 2001; 7:1888-1893.

Beer T M, Ryan C W, Venner P M. Interim results from ASCENT: A double-blinded randomized study of DN-101 (high dose calcitrol) plus docetaxel vs. placebo plus docetaxel in androgen-independent prostate cancer. ASCO Meeting Abstracts. 2005; 23:4516.

Sahoo K. Ma W. Labhasetwar V. Efficacy of transferrin-conjugated paclitaxel-loaded nanoparticles in a murine model of prostate cancer. Int J Cancer. 2004; 112:335-340.

Bander N H, Trabulsi E J, Kostakoglu L. Targeting metastatic prostate cancer with radiolabeled monoclonal antibody J591 to the extracellular domain of prostate specific membrane antigen. J Urol. 2003; 170:1717-1721.

Smith-Jones P M, Vallabhajosula S, Navarro V. Radiolabeled monoclonal antibodies specific to the extracellular domain of prostate-specific membrane antigen: Preclinical studies in nude mice bearing LNCaP human prostate tumor. J Nuc Med. 2003; 44:610-617.

Chang SS. Overview of prostate-specific membrane antigen. Reviews in Urology. 2004; 6(10):S13-18

What is claimed is:

1. An activated polymeric nanoparticle for targeted drug delivery comprising:
   an active agent disposed within a biodegradable nanoshell having a targeting agent, wherein the nanoshell comprises a poly-lactic-co-glycolic acid biocompatible polymer in contact with an amphiphilic polyol stabilizing agent;
   a spacer compound non-covalently sequestered in the nanoshell wall, wherein the spacer is selected from the group consisting of bis(sulfosuccinimidyl)suberate, ethylene glycolbis-(sulfosuccinimidylsuccinate), disuccinimidyl glutarate, N-[e-maleimidocaproyloxy]sulfosuccinimide ester, N-[b-maleimidopropyloxy] succinimide ester, and 1,8-bismaleimidodiethyleneglycol; and
   the targeting agent is bound to the non-covalently sequestered spacer compound such that the targeting agent is displayed on the exterior surface of the nanoshell.

2. The nanoparticle of claim 1, wherein the polyol comprises at least one polyethylene glycol.

3. The nanoparticle of claim 1, wherein the targeting agent selectively targets the nanocarrier to diseased tissue/cells, thereby minimizing whole body dose.

4. The nanoparticle of claim 1, wherein the nanoshell loaded with an active agent combines a conventional radioisotopes and a chemotherapeutic.

5. The nanoparticle of claim 1, wherein the nanoshell is adapted for controlled release of the active agents by pre-determining one or more polymeric ratios of lactic to glycolic acid.

6. The nanoparticle of claim 1, wherein the spacer is heterofunctional.

7. The nanoparticle of claim 1, wherein the active agent comprises a curcumin or curcuminoid.

8. A pharmaceutical agent comprising:
   a pharmaceutically acceptable carrier and
   an activated polymeric nanoparticle comprising an active agent disposed within a biodegradable nanoshell having a targeting agent, wherein the nanoshell comprises a poly-lactic-co-glycolic acid biocompatible polymer in contact with an amphiphilic polyol stabilizing agent;
   a spacer compound non-covalently sequestered in the nanoshell wall, wherein the spacer is selected from the group consisting of bis(sulfosuccinimidyl)suberate, ethylene glycolbis-(sulfosuccinimidylsuccinate), disuccinimidyl glutarate, N-[e-maleimidocaproyloxy]sulfosuccinimide ester, N-[b-maleimidopropyloxy] succinimide ester, and 1,8-bismaleimidodiethyleneglycol, wherein
   the targeting agent is bound to the non-covalently sequestered spacer compound thereby binding the targeting agent to the biodegradable nanoshell exterior surface such that a targeting region is exposed.

9. An activated polymeric nanoparticle for targeted drug delivery comprising:
   an active agent disposed within a biodegradable nanoshell having a targeting agent, wherein the nanoshell comprises
   a poly-lactic-co-glycolic acid biocompatible polymer in contact with a polyvinyl alcohol amphiphilic stabilizing agent;
   a spacer compound non-covalently sequestered in the nanoshell wall, wherein the spacer compound is selected from the group consisting of bis(sulfosuccinimidyl)suberate, ethylene glycolbis-(sulfosuccinimidylsuccinate), disuccinimidyl glutarate, N-[e-maleimidocaproyloxy] sulfosuccinimide ester, N-[b-maleimidopropyloxy]succinimide ester, and 1,8-bismaleimidodiethyleneglycol; and
   the targeting agent connected to the spacer compound thereby binding the targeting agent to the biodegradable nanoshell exterior surface.

10. The nanoparticle of claim 9, wherein the active agent is selected from a curcumin and a curcuminoid.

11. An activated polymeric nanoparticle for targeted drug delivery comprising:
   a biodegradable nanoshell comprising a poly-lactic-co-glycolic acid polymer non-covalently associated with a bis-succinimidyl suberate crosslinking agent in the nanoshell wall, wherein the crosslinking agent extends from the biodegradable nanoshell surface;
   a targeting agent attached to the bis-succinimidyl suberate crosslinking agent; and
   a curcumin active agent disposed within the biodegradable nanoshell.

* * * * *